US008726719B2

(12) United States Patent
Vass et al.

(10) Patent No.: US 8,726,719 B2
(45) Date of Patent: May 20, 2014

(54) LIGHT-WEIGHT ANALYZER FOR ODOR RECOGNITION (75) Inventors: Arpad A. Vass, Oak Ridge, TN (US); Marcus B. Wise, Kingston, TN (US)

(73) Assignee: UT-Battelle, LLC, Oak Ridge, TN (US)

(*) Notice: Subject to any disclaimer, the term of this patent is extended or adjusted under 35 U.S.C. 154(b) by 291 days.

(21) Appl. No.: 12/848,118

(22) Filed: Jul. 31, 2010

(65) Prior Publication Data
US 2012/0024042 A1 Feb. 2, 2012

(51) Int. Cl.
G01N 33/00 (2006.01)
G01N 33/497 (2006.01)

(52) U.S. Cl.
USPC .......................... 73/23.34; 73/23.2; 73/31.05

(58) Field of Classification Search
USPC .............. 73/23.2, 23.34, 31.01, 31.03, 31.05, 73/32.02, 23.3, 31.02
See application file for complete search history.

(56) References Cited

U.S. PATENT DOCUMENTS

| | | |
|---|---|---|
| 2,947,166 A | 8/1960 | Palmer et al. |
| 3,675,466 A | 7/1972 | Linenberg |
| 3,771,349 A | 11/1973 | Yatabe |
| 3,903,726 A | 9/1975 | Hirosawa et al. |
| 4,173,886 A | 11/1979 | Archbold et al. |
| 4,319,482 A | 3/1982 | Bunner |
| 4,399,688 A | 8/1983 | Dennis |
| 4,609,875 A | 9/1986 | Jeffers |
| 4,617,821 A | 10/1986 | Yokoyama et al. |
| 4,736,618 A | 4/1988 | Usami et al. |
| 4,785,658 A | 11/1988 | Jackson |
| 5,014,541 A | 5/1991 | Sides et al. |
| 5,277,057 A | 1/1994 | Takashima et al. |
| 5,284,569 A | 2/1994 | Lee et al. |
| 5,296,196 A | 3/1994 | Takeshima |
| 5,347,223 A | 9/1994 | Krcma et al. |
| 5,363,690 A | 11/1994 | Evangelista et al. |
| 5,371,467 A | 12/1994 | Jeffers |
| 5,435,169 A | 7/1995 | Mitra |
| 5,448,905 A | 9/1995 | Stetter et al. |
| 5,801,297 A * | 9/1998 | Mifsud et al. ................ 73/23.34 |
| 5,922,939 A | 7/1999 | Cota |
| 5,932,176 A | 8/1999 | Yannopoulos et al. |
| 6,341,629 B1 | 1/2002 | Clark et al. |

(Continued)

FOREIGN PATENT DOCUMENTS

WO 0025108 A1 5/2000
WO 2006078255 A1 7/2006

OTHER PUBLICATIONS

Figaro, Technical Information on Usage of TGS Sensors for Toxic and Explosive Gas Leak Detectors, Mar. 2005.

(Continued)

*Primary Examiner* — Randy W Gibson
*Assistant Examiner* — Natalie Huls
(74) *Attorney, Agent, or Firm* — Quarles & Brady LLP (57) ABSTRACT The invention provides a light weight analyzer, e.g., detector, capable of locating clandestine graves. The detector utilizes the very specific and unique chemicals identified in the database of human decompositional odor. This detector, based on specific chemical compounds found relevant to human decomposition, is the next step forward in clandestine grave detection and will take the guess-work out of current methods using canines and ground-penetrating radar, which have historically been unreliable. The detector is self contained, portable and built for field use. Both visual and auditory cues are provided to the operator.

26 Claims, 4 Drawing Sheets

(56) References Cited

U.S. PATENT DOCUMENTS

| | | | |
|---|---|---|---|
| 6,467,332 B1* | 10/2002 | Bertschi et al. | 73/23.34 |
| 6,824,394 B1 | 11/2004 | Brundage | |
| 6,844,197 B1 | 1/2005 | Doleman et al. | |
| 6,952,945 B2 | 10/2005 | O'Brien | |
| 7,003,405 B1 | 2/2006 | Ho | |
| 7,041,256 B2 | 5/2006 | Wang et al. | |
| 7,159,445 B2 | 1/2007 | Bohm et al. | |
| 7,168,423 B2 | 1/2007 | Nonaka | |
| 7,403,113 B2* | 7/2008 | Moon et al. | 340/539.22 |
| 7,533,558 B2 | 5/2009 | Flaherty et al. | |
| 7,571,634 B2 | 8/2009 | Grosse Bley | |
| 7,588,726 B1* | 9/2009 | Mouradian et al. | 422/83 |
| 8,074,490 B2* | 12/2011 | Andrews et al. | 73/31.05 |
| 2002/0026822 A1 | 3/2002 | Reading et al. | |
| 2003/0015019 A1 | 1/2003 | O'Brien | |
| 2004/0016287 A1* | 1/2004 | Fu | 73/23.34 |
| 2004/0053290 A1 | 3/2004 | Terbrueggen et al. | |
| 2004/0069046 A1* | 4/2004 | Sunshine et al. | 73/23.34 |
| 2005/0126264 A1 | 6/2005 | Komninos | |
| 2005/0191757 A1* | 9/2005 | Melker et al. | 436/164 |
| 2006/0191319 A1* | 8/2006 | Kurup | 73/23.34 |
| 2006/0218987 A1* | 10/2006 | Campman | 73/23.2 |
| 2007/0113686 A1* | 5/2007 | Desrochers et al. | 73/863.33 |
| 2007/0241917 A1* | 10/2007 | Tiwet et al. | 340/632 |
| 2008/0028827 A1* | 2/2008 | Andrews et al. | 73/23.2 |

OTHER PUBLICATIONS

Bacharach, Inc., Leakator 10, Instruction 19-9167, Combustible Gas Detector, Rev. 10, May 2002.

Bacharach, Inc., The Informant Refrigerant Leak Detector, Instruction 19-9210, Operation & Maintenance, Rev. 4, Apr. 2001.

Thompson, et al., Effects of Silcosteel Transfer Line on the Sampling of Volatile Organic Compounds, Field Analytical Chemistry and Technology 2(5):309-314, 1998.

Vass, et al., Decompositional Odor Analysis Database, J. Forensic Sci. 49(4):1-10, 2004.

PCT International Search Report and Written Opinion, PCT/US2011/045217, Jan. 3, 2012.

* cited by examiner

LIGHT-WEIGHT ANALYZER FOR ODOR RECOGNITION

STATEMENT REGARDING FEDERALLY SPONSORED RESEARCH

This invention was made with U.S. Government support under Contract No. DE-AC05-00OR22725 between the United States Department of Energy and UT-Battelle, LLC. The United States Government has certain rights in this invention.

CROSS-REFERENCES TO RELATED APPLICATIONS

Not Applicable.

BACKGROUND OF THE INVENTION

1. Field of the Invention

This invention relates in general to a light weight analyzer capable of detecting and recognizing odor volatile chemicals. In particular, the light weight analyzer is capable of detecting clandestine burial sites of human remains and detecting and recognizing odors emitted from human remains, such as decomposed human remains.

2. Description of the Related Art

Locating clandestine graves, identification of victims (development of biological profiles from unidentified persons), and odor recognition (in locating and identifying individuals) are very difficult, costly and time consuming tasks which impact law enforcement, intelligence and military operations around the world.

Locating buried human remains, in particular, is one of the most difficult tasks currently facing archeologists, anthropologists, and law enforcement personnel. Investigations to locate clandestine graves are time consuming and costly. Typical burials are not located in less than 10 years and many of those are either accidental discoveries or are identified by the perpetrator. Many criminal burials occur in remote areas, are typically shallow and are typically wrapped in some type of material. Additionally, the slow diffusion of material from the soil and the length of internment make locating clandestine graves via vegetational changes very challenging.

There are three primary means of locating clandestine graves today: manual probing, ground penetrating radar (GPR), and canines. Many agencies usually employ a combination of all these methods when searching for clandestine graves, mass graves, or missing persons. Manual probing is very inexpensive and is used to locate disturbed soil regions, but cannot confirm the presence of a corpse and can only be used in small areas. Ground-penetrating radar (GPR) has been used for several years as a non-destructive method of locating subsurface anomalies. GPR is usually expensive and also locates areas of disturbed soil. Under ideal conditions, and if the grave is very fresh, GPR can sometimes indicate the presence of a corpse, but objects in the environment (e.g. roots, stumps, rocks, debris, man-made objects, etc.) can yield false-positive results and a significant amount of training is required to interpret the signals indicative of clandestine graves. No matter how the data is processed and visualized, GPR units can only penetrate to a limited depth. As the electromagnetic pulses dissipate with depth, they eventually fade to nothingness.

For centuries, canines have had a well-established and integral part in law enforcement. They have proven to be invaluable in such vital areas as explosive detection, narcotics detection, and tracking and searching for criminals, lost persons and missing persons. The ability of dogs to detect human scent is strongly documented throughout the literature.

Human scent is composed of skin flakes, perspiration, skin oils and gaseous components. Depending upon the task, police canines utilize different aspects of these components. When tracking the scent of a suspect, the canine follows the skin flakes and disturbances to ground vegetation. If the task is article recovery, skin oils of the suspect have contaminated the object being sought. Canines are capable of locating such objects (e.g. guns) up to 48 hours later. For example, police canine can detect a hidden suspect from airborne scents of fatty acids in the skin oils.

It is reported that a comparison of olfactory cell counts between humans and canines indicate that a dog's sense of smell is at least 44 times better. In addition, dogs are able to distinguish the odors of different people, and it is believed that the most probable advantage canines possess is scent discrimination or the ability to distinguish one scent from another. However, a dog's ability to locate gravesites when no physical evidence is present still remains a mystery.

Canines that detect human remains, commonly referred to as human remains detection (HRD) canines, have been minimally represented in the law enforcement canine population across the United States. Their ability to locate as little as 5-15 mg of human tissue, blood, or bone, either buried, on the surface, or elevated above the ground, exceeds the ability of current instrumentation. In addition, it has been reported that HRD canines have identified remains, graves over 100 years old, and minute amounts of human material (even when masked). Given their reported abilities, HRD canines are still not the final answer for grave detection today primarily because of a lack of standardization in their training procedures and a poor understanding of their scenting capabilities. Research has shown that the odor of decomposition changes over time, therefore, an HRD canine trained only on tissue will potentially have a more difficult time detecting bone material since the lack of tissue has caused the composition of the odor signature to change.

Unfortunately, empirical evidence documenting how the canine utilizes their amazing olfactory skills is far from complete and little scientific testing of law enforcement canines has been conducted. The current concern facing cadaver dog units is that training is inadequate since it is unknown to what odor signals the dogs respond to when alerting and the alerting may not completely be in response to odor. This jeopardizes search and seizure as well as probable cause rules currently established for search warrants and chain of custody. Furthermore, it is not feasible for many agencies to have an HRD program.

Forensic chemistry is one of the most important sub-disciplines of forensic science, providing detailed analytical information to investigators of crimes involving drugs, explosives, toxic chemicals and biological substances. Chemical analysis is primarily conducted in laboratories on samples collected in the field or at a crime scene using a "best guess" sampling strategy. Sample turn-around times in the laboratories can be long (many days) and important samples may be missed at the crime scene due to a lack of information during the collection process. Low-cost chemical sensing equipment that is easy to operate would significantly enhance the ability of crime scene investigators to locate and collect samples, avoid missing critical evidence, and reduce the number of times that a site must be revisited to collect additional samples.

U.S. Patent Application Publication No. 2008/0028827 describes a significant advance in methods and devices for detecting a burial site of human remains. In view of the advances in the art provided by the device of U.S. Patent Application Publication No. 2008/0028827, even further improvements to this technology would be beneficial.

SUMMARY OF THE INVENTION

The need for an improved method and apparatus for detecting clandestine burial sites of human remains is met by the present invention. An odor recognition apparatus according to the invention features a significant number of improvements and greater versatility compared to prior devices. The odor recognition apparatus is a hand-held, battery powered sensor system configured similar to a metal detector.

In one version, the odor recognition apparatus utilizes an array of twelve heated metal oxide sensors optimized for the detection of the major classes of volatile chemicals known to be present during various stages of human decomposition. This significantly improves the ability to discriminate between human decomposition odor and chemical vapors (interferences) present in the environment. Additional sensors, including sensors with orthogonal detection capability can be easily added to the system without increasing the complexity of the signal processing electronics or the computer interface.

The cost in relation to prior sensor systems has been reduced through the use of a sensor modulation scheme in which each sensor is modulated with a unique audio frequency. The audio frequency tones are pure sine waves. This means that there is only one frequency component applied to each individual sensor. These audio frequency tones are electronically combined into a composite audio signal that is output to both an audio amplifier and the audio input of a computer sound card or some other analog to digital converter interface. The actual computer interface is therefore a standard shielded stereo audio cable. The computer and computer sound card are used to digitize and store the data and a Fast Fourier Transform software program is used to decipher the composite audio stream into the signal responses for each sensor.

The sensor drive signals can be adjusted to correlate to traditional music notes in the musical key of "C" (or any other musical key) in equal temperament tuning. There are twelve sensors in one non-limiting example system which covers 1½ octaves starting at 220 Hz (key 37 on the piano, A3) through 659.255 Hz (key 56 on the piano, E5). The combined audio signal is therefore "musical" in nature as the musical chords produced will depend on the relative response of each sensor to a particular chemical vapor. This composite audio signal (music) is amplified and output to a pair of speakers so that the instrument operator has an audible indication of the presence of chemical vapors as well as an audible cue of what type of vapors are present.

In one embodiment, a visual indication of the response of each sensor is provided by bar graphs on a front display panel of the odor recognition apparatus. The bar graph display essentially corresponds to the "power spectrum" of the combined audio signal (although they are driven through a simple analog processing of the signals). This display is very similar to the power spectrum produced on the computer after Fast Fourier Transform of the time domain composite audio signal. The combined audio output and visual output built into the odor recognition apparatus allow the instrument operator to use the odor recognition apparatus independently of a computer if desired. Data can be saved either by recording the audio with a computer or simply by recording the data with a small, hand-held or portable digital audio recorder. The odor recognition apparatus is compatible and easily upgradeable with additional sensors simply by including an additional audio frequency oscillator and sensor modulator into the electronics for each new sensor added. Additionally, the Fourier Transformed Data can be processed by a computer using pattern recognition programs to provide an improved ability to identify a particular chemical vapor.

The odor recognition apparatus is a chemical vapor sensing system that relies on the ability to sample chemical vapors just above soil or in a hole dug into the soil. Greater versatility for this type of sampling has been incorporated by providing interchangeable vapor sampling inlets and an active sample flow path with adjustable sample flow volume. This also increases the versatility of the unit for other applications. The odor recognition apparatus electronics, sensor modulation scheme and physical construction are highly compatible with additional sensing technologies that are potentially useful for detecting clandestine graves. These include metal detector heads, fluorescence excitation and detection probes (for bone fragments), audio imaging (sonar), infrared and visible video imaging, soil conductivity probes and ground penetrating radar (GPR). The odor recognition apparatus is directly compatible with Global Positioning System (GPS) electronics for identifying and recording locations accurately. The modular construction of the odor recognition apparatus allows the configuration to be easily changed for other applications in addition to searching for clandestine graves. These include but are not limited to drug detection, clandestine drug laboratory testing, pollution detection, and numerous forensics applications such as accelerant detection during arson investigations. Samples from potential sites in the field can be archived with the odor recognition apparatus either on scent pads or using chemical sorbent traps for subsequent laboratory analysis. The odor recognition apparatus can be in any configuration (e.g., backpack version etc.) and can be used for any volatile signature. The odor recognition apparatus does not have to battery operated and can be configured to plug into an outlet or generator, etc. Certain features such as GPS electronics can be added if desired.

In one aspect, the invention provides an array of multiple chemical sensors in which the specific sensors have been selected or optimized for the major chemicals or classes of chemicals that are known to be present at various stages of human decomposition.

In another aspect, the invention provides a chemical sensor array in which the output of each individual sensor may be turned on or off at any time during operation. In one version of the chemical sensor array, the response of each individual sensor is continuously displayed on a bar graph format. In another version of the chemical sensor array, the array outputs are used collectively as an electronic nose and individually at the same time for the identification of chemical vapors.

In yet another aspect, the invention provides a sensor modulation scheme for driving each sensor in a chemical sensor array with a unique audio frequency tone. In one version of the sensor modulation scheme, each sensor in the array is driven with a pure sine wave containing only a single frequency component with no harmonic components. The sine waves can be produced by an oscillator. In another version of the sensor modulation scheme, each sensor in the array is driven with a pure sine wave that is adjustable in amplitude from near zero (0) volts peak-to-peak to a level of up to 100 volts peak-to-peak. In another version of the sensor modulation scheme, each sensor in the array is driven with a pure sine wave that can be offset with either a positive or negative voltage with respect to signal ground. In another version of the sensor modulation scheme, each sensor in the array is driven with a pure sine wave that is completely positive with respect to signal ground. In another version of the sensor modulation scheme, each sensor in the array is driven with a pure sine wave that is completely negative with respect to signal ground. In another version of the sensor modulation scheme, each sensor in the array is driven with a pure sine wave that is an alternating current signal respect to signal ground in which the positive and negative cycles can be either balanced or unbalanced in amplitude with respect to signal ground. In another version of the sensor modulation scheme, each sensor in the array is driven with pure sine waves that may include a mixture of offset voltages (positive, negative, or alternating polarity) with respect to signal ground. In another version of the sensor modulation scheme, each sensor in the array is driven with a unique audio frequency that corresponds to musical notes. In another version of the sensor modulation scheme, each sensor in the array is driven with unique audio frequencies where the audio frequencies comprise a sequential musical notes on an octave scale. In another version of the sensor modulation scheme, the scheme produces a pure sine wave at the output of a sensor that is proportional in amplitude to the response of a sensor to a chemical vapor. In another version of the sensor modulation scheme, the scheme produces a musical note at the output of the sensor where the loudness of the note is proportional to the response of the sensor to a chemical vapor.

In still another aspect, the invention provides a chemical sensor modulation and detection scheme for directly modulating chemical sensors with a pure sine wave and producing a sine wave at the sensor's output whose amplitude is directly proportional in to the response of the sensor to the presence of chemical vapors. Some examples of sensor types that are compatible with this scheme include: heated metal oxide sensors (Taguchi sensors), capacitive sensors, light emitting diode/photo diode sensors, catalytic bead sensors, solid-state sensors, resistive sensors, thermocouples, thermal resistors, and platinum resistors, cantilevers, among others.

In yet another aspect, the invention provides a chemical sensor modulation and detection scheme for modulating a chemical sensor's output with a pure sine wave in order to generate a pure sine wave whose amplitude is directly proportional to the response of the sensor to the presence of chemical vapors. This includes the use of a separate modulation device such as a mixer or a voltage controlled amplifier to generate an amplitude modulated sine wave from sensors that cannot be directly modulated. Some examples of sensor types that are compatible with this scheme include: electrochemical cells, chromatograph detectors, humidity sensors, metal detection sensors, and stand alone sensors packages that produce an output that is not already in the form of a pure sine wave.

In still another aspect, the invention provides a sensor array data fusion method in which the outputs of all sensors are unique sine waves and are electronically mixed to produce a composite signal. In one version of the sensor array data fusion method, the outputs of new sensors can be readily fused with the existing sensors simply by modulating the output of the new sensor at a unique frequency and electronically mixing the signal with those of the existing sensors. In another version of the sensor array data fusion method, the outputs of individual sensors may be included or excluded from the fused data stream at any time by the system operator. In another version of the sensor array data fusion method, the outputs from different groups of sensors may be fused into separate data streams for simplifying data interpretation or for increased dynamic range of the response. In another version of the sensor array data fusion method, the fused data are a composite audio signal of the proper electrical characteristics for transmission to a computer or data recording device through a 2 or 3 wire shielded audio cable. In another version of the sensor array data fusion method, the fused data are a composite audio signal of the proper electrical characteristics for direct input into the audio input port of a personal computer.

In yet another aspect, the invention provides a sensor array data storage method in which the combined sensor data are digitized and stored as a wave file (*.wav). In one version of the sensor array data storage method, the combined sensor data are digitized and stored as any type of computer file that can be converted to a format that is compatible with a Fast Fourier Transform software program.

In yet another aspect, the invention provides a sensor array data de-convolution method that recovers the response of each individual sensor by performing a Fast Fourier Transform on a composite audio signal that is comprised of the sine wave outputs of each sensor. In one version of the sensor array data de-convolution method, audio processing software is used to extract the response of the individual sensors. In one version of the sensor array data de-convolution method, audio frequency band-pass filter software is used to extract the response of the individual sensors.

In still another aspect, the invention provides a sensor array data processing method that utilizes pattern recognition software applied to de-convoluted sensor data from the sensor array data de-convolution method to identify chemical vapors detected by the sensors. In one version of the sensor array data processing method, the method is executed by means of a microprocessor built into the sensor unit that utilizes pattern recognition software applied to de-convoluted sensor data from the sensor array data de-convolution method to identify chemical vapors detected by the sensors.

In yet another aspect, the invention provides a sensor array data output method in which the data are electronically fused into either one or two channels of audio frequency data that can be directly amplified and output using audio speakers or headphones operated in either a "monophonic" or "stereo" mode. In one version of the sensor array data output method, the data are electronically fused into either one or two channels of audio frequency data that can be directly amplified and output using audio speakers and the loudness of the audio signal is directly proportional to the response of the sensors to the presence of chemical vapors. In another version of the sensor array data output method, the data are electronically fused into either one or two channels of audio frequency data that are comprised of musical notes that can be directly amplified and output using audio speakers or headphones and where the loudness of the audio signal is directly proportional to the response of the sensors to the presence of chemical vapors. In another version of the sensor array data output method, the data are electronically fused into either one or two channels of audio frequency data that are comprised of musical notes that can be directly amplified and output using audio speakers or headphones and where the relative amplitude of each musical note is directly proportional to the response of each sensor to the chemical vapors. In another version of the sensor array data output method, the data are electronically fused into either one or two channels of audio frequency data that are comprised of musical notes that can be directly amplified and output using audio speakers or headphones and where the outputs of each individual sensor can be readily included or excluded by the instrument operator. In another version of the sensor array data output method, the method includes simultaneous output of combined audio signals, bar graph displays of the individual sensor outputs, and a composite data stream for audio recording or computer interfacing. In another version of the sensor array data output method, the method includes the simultaneous output of combined audio signals, bar graph displays of the individual sensor outputs, and a composite data stream for audio recording or computer interfacing wherein any sensor or combination of sensors in the array may be included or excluded from the data output.

In still another aspect, the invention provides a chemical sensor array that can be used either as a static vapor detector (no air flow across the sensors) or as a dynamic vapor detector (with active air flow across the sensors). In one version of the chemical sensor array, there is active air flow where the amount air flow can be varied and optimized by the system operator. In another version of the chemical sensor array, there is active air flow where a portion of the vapor stream is archived on a chemical scent pad or a chemical sorbent trap for subsequent analysis in a laboratory or for use with scent-detecting canines. In another version of the chemical sensor array, there is active air flow that incorporates interchangeable vapor sampling hoods, shrouds, tubes, and probes for optimal use in locations where the surface soil gas vapors are not readily accessible due to vegetation, rocks, man-made objects, holes, or other obstacles. In another version of the chemical sensor array, there is active air flow that incorporates interchangeable wind screens to minimize the depletion of surface soil vapors by wind turbulence. In another version of the chemical sensor array, the system is assembled in a modular manner so that it can be easily reconfigured for different chemical detection uses. In another version of the chemical sensor array, the system that can be readily configured for specific applications including the detections of clandestine graves, hidden drugs, hidden explosives, chemical pollutants, toxic materials, combustion accelerants or any other type of volatile chemical signature from any source. In another version of the chemical sensor array, the individual sensors may be interchanged with other sensors of the same or similar type for specific applications and sensing requirements. In another version of the chemical sensor array, the individual sensors include a mixture of different sensor types including but not limited to heated metal oxide sensors, non-dispersive infrared sensors, electrochemical sensors, coated surface acoustic wave sensors, solid state microcantilever sensors, photoionization sensors, ultraviolet sensors, visible light sensors, ionization sensors, semiconductor sensors, and ion mobility sensors among others.

In yet another aspect, the invention provides a chemical sensor system that incorporates a GPS (Global Positioning System) unit for determining the location of chemical data produced by the chemical sensors. In still another aspect, the invention provides a chemical sensor system that incorporates a bar graph display that is proportional to the combined output of all of the sensors. In yet another aspect, the invention provides a chemical sensor array system that has the ability to differentiate between the chemical vapors of human decomposition and animal decomposition. In still another aspect, the invention provides a chemical sensor array system that has the ability to differentiate between the chemical vapors of human decomposition and presence of chemical vapors from natural or man-made sources.

In still another aspect, the invention provides a chemical sensor array that includes temperature and humidity sensors for compensation of the chemical sensor outputs due to changes in temperature, humidity, or both.

In yet another aspect, the invention provides a chemical sensor array combined with a metal detector where the metal detector excitation and search coils are co-located with the vapor inlet for the chemical sensors.

In still another aspect, the invention provides a chemical sensor array combined with a video camera and video recording device to produce a visual record of where chemical vapors are detected and where the video data and chemical data are time correlated.

In yet another aspect, the invention provides a chemical sensor array combined with a light source that is capable of producing visible light fluorescence from bones, fragments of bones, or teeth when the light is projected on an area adjacent to the chemical vapor inlet of the chemical sensor array.

In still another aspect, the invention provides a chemical sensor array combined with a light source and photolytic detector that is capable of generating and detecting visible light fluorescence from bones, fragments of bones, or teeth when the light is projected on an area adjacent to the chemical vapor inlet of the chemical sensor array.

In yet another aspect, the invention provides a chemical sensor array combined with a light source and photolytic detector that is capable of generating and detecting visible light fluorescence where the output of the detector is modulated with a pure audio frequency sine wave.

In still another aspect, the invention provides a chemical sensor array combined with an infrared video camera and recorder where the data from the chemical sensors and infrared video camera are time correlated.

In yet another aspect, the invention provides a chemical sensor array combined with a thermal imaging camera and recorder and where the data from the chemical sensors and thermal imaging camera are time correlated.

In still another aspect, the invention provides a chemical sensor array combined with an audio probe for detecting subsurface objects located in the immediate vicinity of the chemical vapor inlet of the chemical sensor array.

In yet another aspect, the invention provides a chemical sensor array combined with a soil resistance probe for detecting changes in soil resistance in the immediate vicinity of the chemical vapor inlet of the chemical sensor array.

In still another aspect, the invention provides a chemical sensor array combined with a LASER Induced Breakdown (LIBS) spectrometry probe for detecting inorganic elements at locations immediately adjacent to the chemical vapor inlet of the sensor array.

In yet another aspect, the invention provides a chemical sensor array that includes a combination of heated metal oxide sensors and electrochemical sensors where the outputs of all of the sensors are amplitude modulated pure sine waves each with a unique frequency.

In still another aspect, the invention provides a chemical sensor array that includes a combination of heated metal oxide sensors and capacitive sensors where the outputs of all of the sensors are amplitude modulated pure sine waves each with a unique frequency.

In yet another aspect, the invention provides a chemical sensor array that includes a combination of heated metal oxide sensors and catalytic bead sensors where the outputs of all of the sensors are amplitude modulated pure sine waves each with a unique frequency.

In still another aspect, the invention provides a chemical sensor array that includes a combination of heated metal oxide sensors and infrared chemical sensors where the outputs of all of the sensors are amplitude modulated pure sine waves each with a unique frequency.

In yet another aspect, the invention provides a chemical sensor array that includes a combination of heated metal oxide sensors and visible-light chemical sensors where the outputs of all of the sensors are amplitude modulated pure sine waves each with a unique frequency.

In still another aspect, the invention provides a chemical sensor array that includes a combination of heated metal oxide sensors and solid-state chemical sensors where the outputs of all of the sensors are amplitude modulated pure sine waves each with a unique frequency.

In yet another aspect, the invention provides a chemical sensor array that includes a combination of heated metal oxide sensors and surface acoustic wave chemical sensors where the outputs of all of the sensors are amplitude modulated pure sine waves each with a unique frequency.

In still another aspect, the invention provides a chemical sensor array that includes a combination of heated metal oxide sensors and coated piezo-electric sensors where the outputs of all of the sensors are amplitude modulated pure sine waves each with a unique frequency.

In yet another aspect, the invention provides a chemical sensor array that includes a combination of heated metal oxide sensors and ionization-type chemical sensors where the outputs of all of the sensors are amplitude modulated pure sine waves each with a unique frequency.

In still another aspect, the invention provides a chemical sensor array that includes a combination of heated metal oxide sensors and colorimetric chemical sensors where the outputs of all of the sensors are amplitude modulated pure sine waves each with a unique frequency.

In yet another aspect, the invention provides a chemical sensor array that includes a combination of heated metal oxide sensors and spectroscopic chemical sensors where the outputs of all of the sensors are amplitude modulated pure sine waves each with a unique frequency In still another aspect, the invention provides a chemical sensor array that includes any combination of sensor technologies where the outputs of the chemical sensors are in the form of amplitude modulated sine waves with each sensor having a unique discrete frequency.

In yet another aspect, the invention provides a chemical sensor array system that has a unique marker frequency that can be manually injected into the sensor data output by the system operator to tag data that are deemed especially important.

In still another aspect, the invention provides a chemical sensors array system that incorporates a means of manually nulling (zeroing) each of the sensors in an atmosphere that contains low levels of chemical vapors.

In yet another aspect, the invention provides a chemical sensors array system that incorporates a built-in source of clean air (zero air) for nulling the sensors in an atmosphere that contains levels of chemical vapors of significant enough concentration to interfere with the normal sensor nulling process.

In still another aspect, the invention provides a chemical sensor array that incorporates both automatic and manual nulling of the sensors and in which the nulling mode can be selected by the system operator.

In yet another aspect, the invention provides a chemical sensor array system that produces an audio alerting tone that consists of a single frequency audio tone and where the loudness of the tone is directly proportional to the combined response of all of the sensors.

In still another aspect, the invention provides a chemical sensor array system that produces an audio alerting signal that consists of a tone of fixed amplitude and where the frequency of the tone varies proportionally to the combined response of all of the sensors.

In yet another aspect, the invention provides a chemical sensor array system that produces an audio alerting signal where the output signal has a user adjustable "turn on" threshold analogous to an audio "Squelch" function.

In still another aspect, the invention provides a chemical sensor array system that produces an audio alerting signal consisting of a "chirp" when the sensor output detects a chemical vapor.

In yet another aspect, the invention provides a chemical sensor array system that produces an audio alerting signal consisting of a "chirp" and where the repetition rate of the chirp is proportional to the amount of a chemical vapor detected by the combined chemical sensors.

In still another aspect, the invention provides a chemical sensor array system that has multiple audio alerting options that are selectable by the system operator.

In yet another aspect, the invention provides a chemical sensor array with active air flow controller that automatically selects and adjusts the optimal amount of air flow to achieve the best sensor response.

In still another aspect, the invention provides a chemical sensor array system with user selectable sensitivity for the bar graph display.

In yet another aspect, the invention provides a chemical sensor array system with a means of thermally liberating vapors from soil, such as a heat lamp or hot air blower.

In still another aspect, the invention provides a chemical sensor array system in which the outputs of the individual sensors are unique audio frequency sine waves and combined into a composite audio signal that transmitted to a computer by means of a wireless connection (radio frequency transmitter or infrared transmitter).

In yet another aspect, the invention provides a chemical sensor array system in which the outputs of the individual sensors are unique audio frequency sine waves and combined into a composite audio signal that is synchronized (time correlated) with a second audio signal that contains voice information from the instrument operator (for recording notes, observations, weather conditions, unusual environmental factors, etc).

Thus, it is an advantage of the present invention to provide an apparatus for detecting burial sites of human remains.

It is another advantage to provide a method for detecting a burial site of human remains.

These and other features, aspects, and advantages of the present invention will become better understood upon consideration of the following detailed description, drawings and appended claims.

DETAILED DESCRIPTION OF THE INVENTION

The invention provides an apparatus and a method for detecting a burial site of human remains. An air stream is drawn through an air intake conduit from locations near or above potential sites of human remains. As used herein the term "near or above" means that an air stream can be drawn through an air intake conduit from at least a few centimeters, to at least an inch or more, or one or more feet, from a potential site of human remains. The air stream is monitored by one or more metal oxide sensors to determine whether the air stream includes one or more chemical compounds (e.g., chemical vapors). The presence of certain chemical vapors in the air stream indicates that a burial site of human remains may be present.

Non-limiting examples of chemical compounds liberated during the human decomposition process can include: (1) cyclic hydrocarbons such as 1,4 dimethyl benzene; 1,2 dimethyl benzene; ethyl benzene; toluene; styrene; 1-methyl-2-ethyl benzene; and C4-benzene; (2) non-cyclic hydrocarbons such as heptane; 2-methyl pentane; and undecane; (3) nitrogen compounds such as methenamine; and benzonitrile; (4) sulfur compounds such as sulfur dioxide; carbon disulfide; benzothiazole; 2,4-dimethylthiane, S,S-dioxide; dimethyl trisulfide; and dimethyl disulfide; (5) acid/ester compounds such as hexadecanoic acid; and methyl ester; (6) oxygen compounds such as decanal; benzene methanol; a,a dimethyl; 1-hexanol, 2-ethyl; benzaldehyde; nonanal; benzene (1-methoxypropyl); and 2-propanone; (7) halogen compounds such as trichloromonofluoromethane; chloroform; trichloroethene; tetrachloroethene; dichlorodifluoromethane; dichlorotetrafluoroethane; trichloroethane; and carbon tetrachloride; and (8) naphthalene-containing compounds such as 1-methyl naphthalene; and naphthalene.

Referring now to FIGS. 1 to 4, there is shown an odor recognition apparatus 10 in accordance with a non-limiting example embodiment of the invention. The apparatus 10 is configured for detecting the chemical compounds (e.g., chemical vapors) of human decomposition. The chemical vapors of human decomposition can be, for example, from buried remains or clandestine grave. The human body liberates over 400 chemicals as we revert back to the dust from whence we came. These volatile organic compounds, amino acids, inorganic constituents, and noxious gases are released from a decaying body at specific time points and in specific ratios. This 'chemical signature' can uniquely characterize the state of decomposition. A prototype according to FIGS. 1 to 4 was built as an electronic sniffing tool, which can be referred to as a "Light-weight Analyzer for Buried Remains and Decomposition Odor Recognition". The odor recognition apparatus 10 locates and identifies buried human remains based on their chemical signature. The odor recognition apparatus 10 'sniffs' the volatile compounds generated from these buried remains, and rather than barking as a human remains detection canine, the odor recognition apparatus 10 responds with visual and auditory cues to help pinpoint the hidden grave. In one application, the odor recognition apparatus 10 is used as an augmentation to other cadaver-locating tools such as cadaver dogs, geophysical measurements (magnetometers, soil resistivity, ground penetrating radar, metal detectors), and other such tools.

While the odor recognition apparatus 10 embodied in the prototype is particularly designed to be used in locating human remains from acts of terrorism, genocide, accidents, and natural disasters, the odor recognition apparatus 10 capabilities are not limited to clandestine grave detection. The instrument also can be used in detecting narcotics, accelerants used in arsons, explosives, and other odors (volatile chemicals).

The odor recognition apparatus 10 of FIGS. 1 to 4 includes a main output head 11 having twelve individual sensor selection switches 1a, 2a, 3a, 4a, 5a, 6a, 7a, 8a, 9a, 10a, 11a, and 12a, which turn on and off sensors described below. The main output head 11 also has twelve sensor null adjustment knobs 1b, 2b, 3b, 4b, 5b, 6b, 7b, 8b, 9b, 10b, 11b, and 12b. The main output head 11 also has a sensor response display 12 with twelve individual visual bar graph displays 1c, 2c, 3c, 4c, 5c, 6c, 7c, 8c, 9c, 10c, 11c, and 12c associated with each of the sensors described below. The main output head 11 also has a power switch 14 and a fan speed knob 16. The main output head 11 also has a computer interface summing amplifier selector switch 18.

Figure 3:
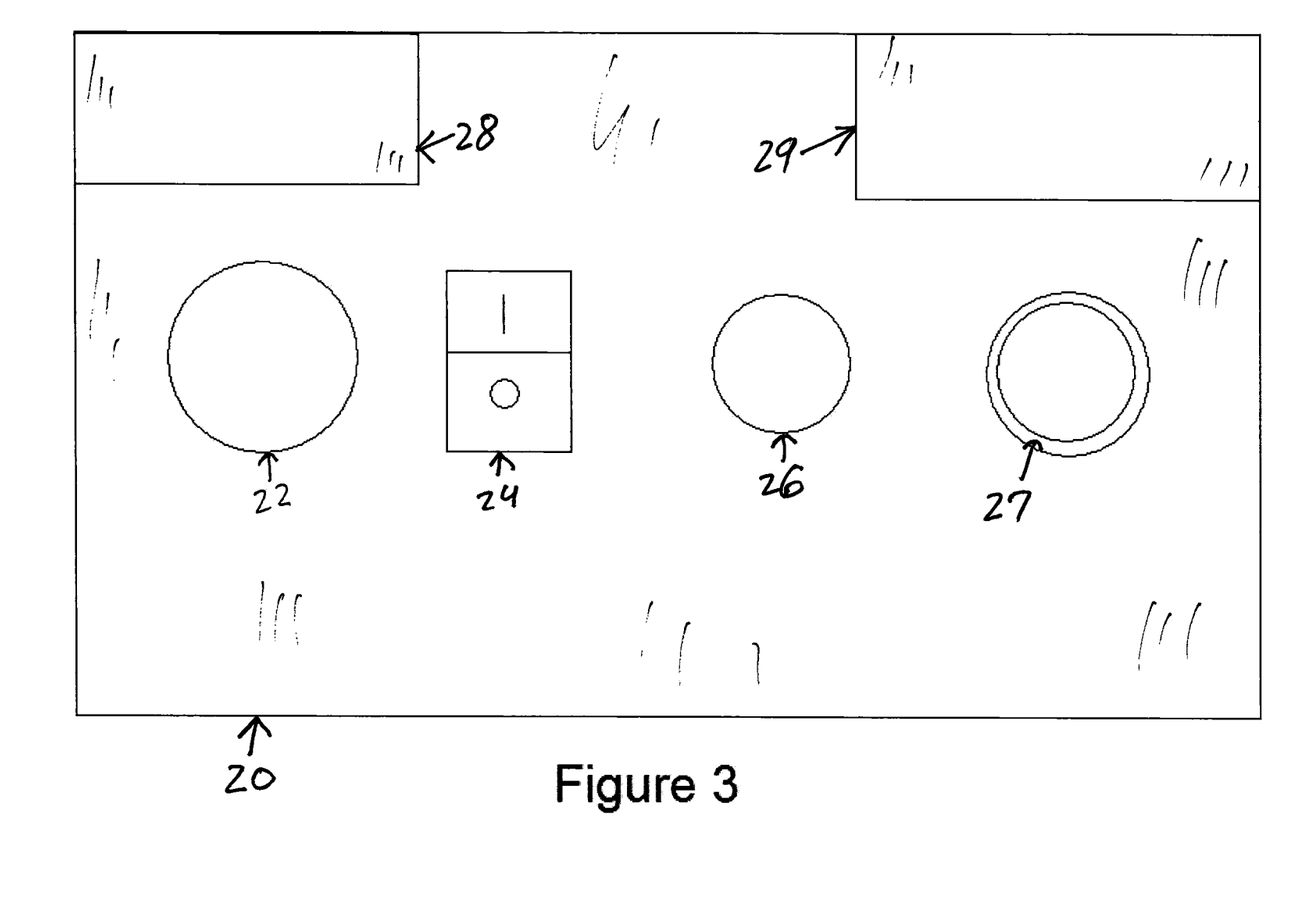
FIG. 3 is a top view of the audio output module of the odor recognition apparatus of FIG. 1.

The odor recognition apparatus 10 includes an audio output module 20 having a volume knob 22, a stereo/mono switch 24, a mute button 26, an audio output jack 27 for headphones, a left speaker 28, and a right speaker 29. The odor recognition apparatus 10 also includes an oscillator module 30 that houses an electronic circuit that produces multiple sine waves of unique frequencies.

The odor recognition apparatus 10 includes a detector head 40 having a nozzle 42 forming a probe head. The nozzle 42 forms part of an air intake conduit 44 that runs from the nozzle 42 through a sensor manifold 46 to a fan 48 and out of an exhaust tube 52. The fan 48 draws an air stream through the nozzle 42 (see arrow A in FIG. 4) and a particulate filter 51 and through the air intake conduit 44. The air stream then exits through the exhaust tube 52 (see arrow B in FIG. 4). In an alternative embodiment, the fan 48 is replaced with a pump for drawing an air stream through the air intake conduit 44. In the sensor manifold 46, there are positioned twelve sensors 56a, 56b, 56c, 56d, 56e, 56f, 56g, 56h, 56i, 56j, 56k and 56l that are in electrical communication with an electronics circuit board (now shown) which is in electrical communication with an electronics circuit (now shown) of the oscillator module 30 via electrical line 62. The oscillator module 30 is in electrical communication with an electronics circuit board (now shown) of the audio output module 20 via electrical line 64. The audio output module 20 is in electrical communication with an electronics circuit board (now shown) of the main output head 11 via electrical line 66.

Figure 1:
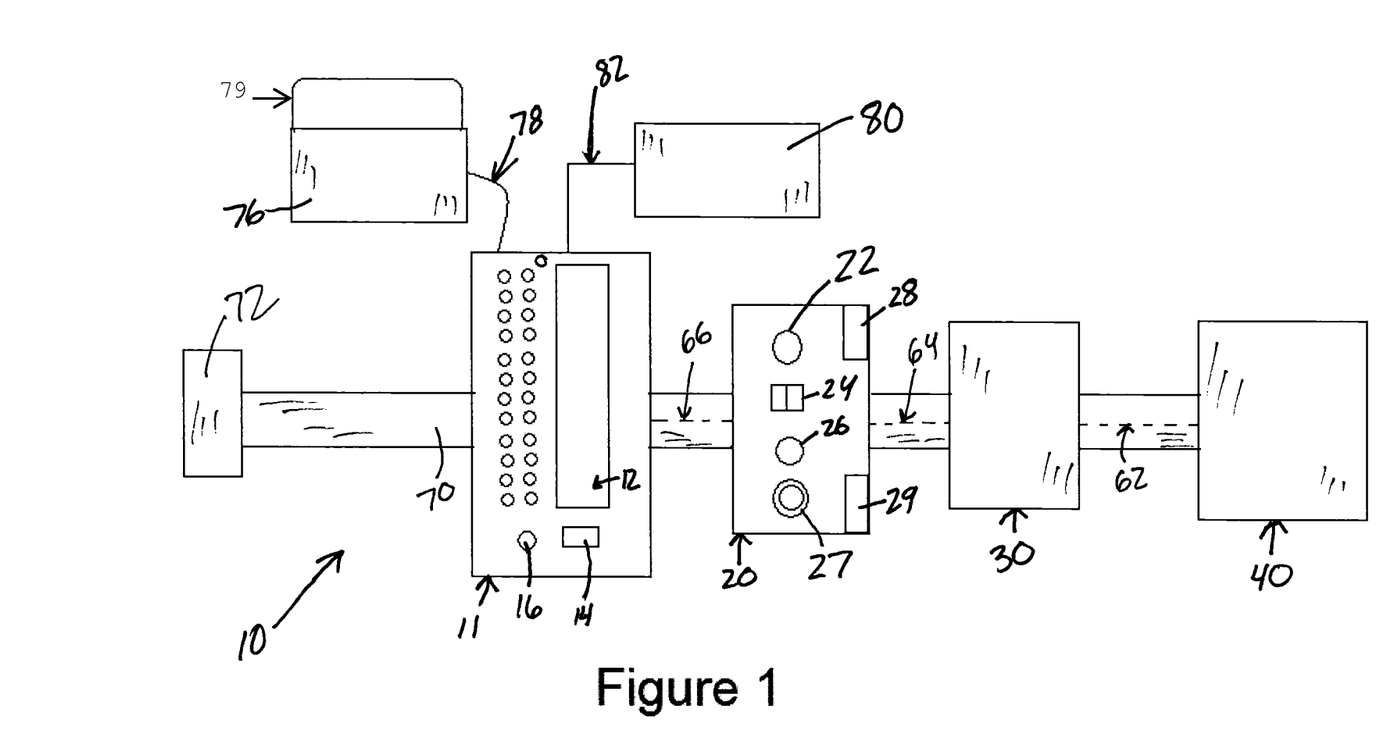
FIG. 1 is a top view of an example odor recognition apparatus according to the invention.

The odor recognition apparatus 10 includes a hollow tubular shaft 70 with a handle 72. The main output head 11, the audio output module 20, the oscillator module 30, and the detector head 40 are attached to the shaft 70 with appropriate brackets and bolts. Ribbon electrical cables connect mating connectors on (a) the main output head 11 and oscillator module 30; (b) the main output head 11 and the detector head 40; (c) the oscillator module 30 and the detector head 40; and (d) the main output head 11 and the audio output module 20. The main output head 11 is connected to a battery supply 76 via electrical line 78. The battery supply 76 can have a carrying strap 79. An external laptop or desktop computer 80 may be connected by an auxiliary computer interface cable 82 to an audio input port of the main output head 11.

Use of the odor recognition apparatus 10 begins by turning on the power switch 14 located on the upper right side of the main output head 11. Four LEDs light up. These LEDs are located (1) above the power switch 11 on the main output head 11, (2) above the volume knob 22 on the audio output module 20, and (3 & 4) on top of the detector head 40. If any of the LEDs are not lit, a user turns off the power and check the connectors of the cables. The user then turns all twelve sensor selection switches 1a, 2a, 3a, 4a, 5a, 6a, 7a, 8a, 9a, 10a, 11a and 12a, to the "On" position. An audible signal should be present and the bar graph displays 1c, 2c, 3c, 4c, 5c, 6c, 7c, 8c, 9c, 10c, 11c, and 12c, indicate some level of response. However, the sensor bar graph outputs have not been "nulled" at this point in time and will likely drift for several minutes during the initial warm-up period. The user adjusts the fan speed knob 16 clockwise to turn on the fan 48 (or pump).

The audio volume can be adjusted to a comfortable audible level using the volume knob 22. The mute button 26 can be used to decrease the volume without changing the audio level setting. While muted, a red LED will flash continuously. Muting can be turned on or off simply by pressing and releasing the mute button 26. Depending on user preference, either a MONO or STEREO audio signal can be selected by the stereo/mono switch 24 located on the audio output module 20. In the "Stereo" mode, the audio output from sensors 56a, 56c, 56e, 56g, 56i, 56k is output to the left speaker 28, while the audio output from sensors 56b, 56d, 56f, 56h, 56j and 56l is output to the right speaker 29. In the "Mono" mode, the audio signals from all sensors 56a, 56b, 56c, 56d, 56e, 56f, 56g, 56h, 56i, 56j, 56k and 56l, are output from both speakers 28, 29 at the same time. The "Stereo" mode can be used to provide a greater range of audible patterns for the instrument operator to employ in determining the nature of a chemical signature. The "Stereo" feature works best if headphones are used instead of the attached left speaker 28 and right speaker 29.

Figure 2:
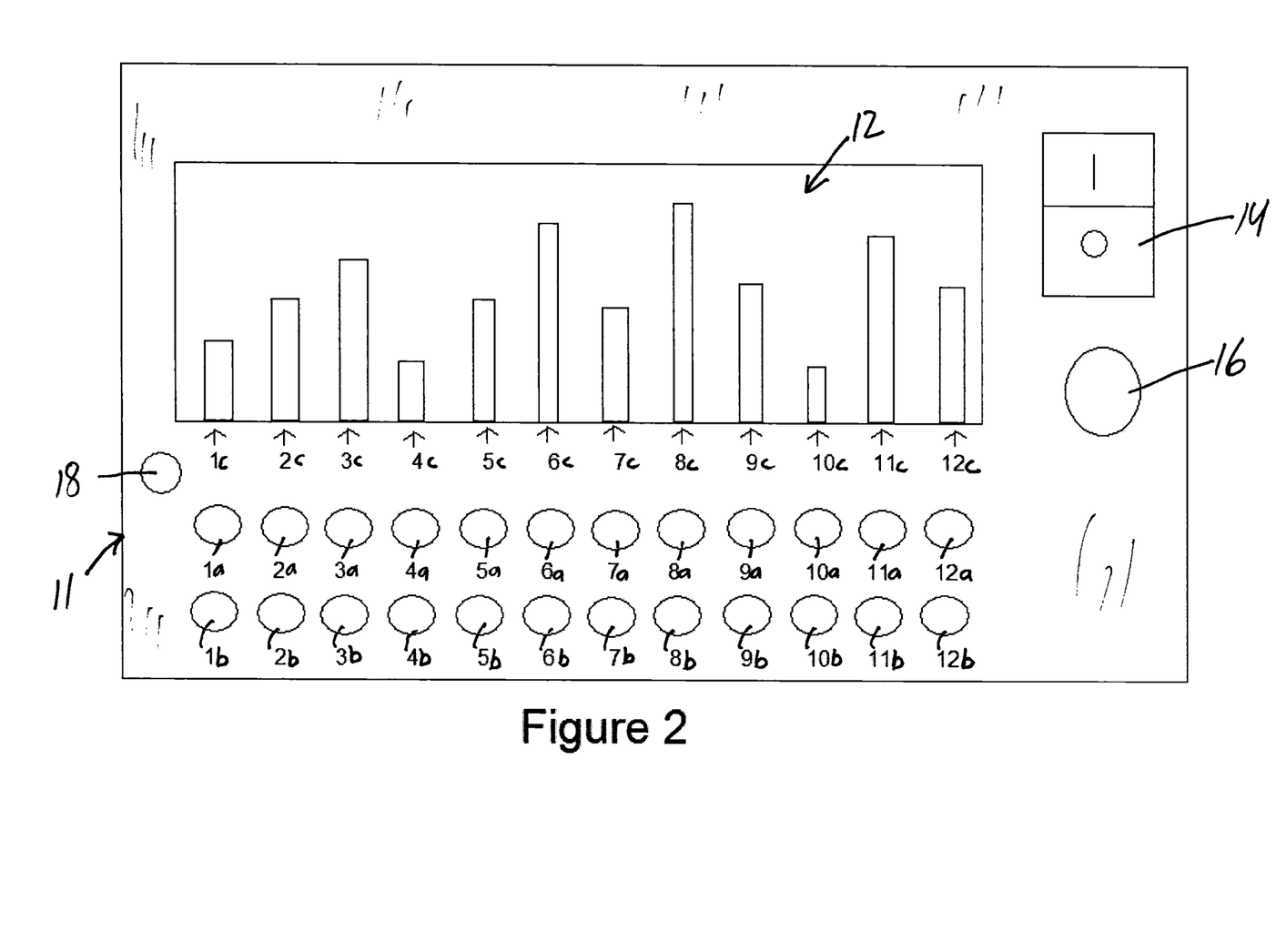
FIG. 2 is a top view of the main output head of the odor recognition apparatus of FIG. 1.

A similar treatment of the audio signals is used for the computer interface. A switch located on the front panel of the main output head 11 allows the external computer to monitor either two channels of information (odd and even sensors) or one channel of combined information. The "2-channel" mode provides greater dynamic range and is less prone to signal distortion and the generation of spurious frequency signals. However, under normal conditions, the selector switch can be set for "1 channel" of information.

After turning on the odor recognition apparatus 10, the odor recognition apparatus 10 should be zeroed or nulled in the ambient environment in which it will be used. Preferably, zeroing is conducted in a location away from sources of man-made or natural chemical vapors. This includes any highly odorous sources such as aromatic vegetation, decomposing waste, solvents, gasoline, petroleum products, fresh paint, etc. If re-zeroing is required during use, it should be conducted in the same location if possible. In the zeroing process, the user starts with sensor 56a and slowly rotates the sensor null adjustment knob 1b in the direction necessary to decrease the level of the signal indicated on the corresponding bar graph display 1c. The user rotates the sensor null adjustment knob 1b until the corresponding sensor bar graph display 1c no longer indicates a response (no segments lit). The user repeats this process for each remaining sensor 56b, 56c, 56d, 56e, 56f, 56g, 56h, 56i, 56j, 56k and 56l using sensor null adjustment knobs 2b, 3b, 4b, 5b, 6b, 7b, 8b, 9b, 10b, 11b and 12b respectively until the bar graph displays 2c, 3c, 4c, 5c, 6c, 7c, 8c, 9c, 10c, 11c, and 12c show no response on any sensor.

Next, the user turns all sensor selection switches 2a, 3a, 4a, 5a, 6a, 7a, 8a, 9a, 10a, 11a, and 12a to the "OFF" position except for sensor selection switch 1a. If the user can hear sound, the user adjusts the sensor null adjustment knob 1b until very little or no sound can be heard. The user repeats this step consecutively with all twelve sensors 56a, 56b, 56c, 56d, 56e, 56f, 56g, 56h, 56i, 56j, 56k and 56l using sensor selection switches 2a, 3a, 4a, 5a, 6a, 7a, 8a, 9a, 10a, 11a, and 12a respectively. The user adjusts making sure only one sensor at a time is turned ON during this process. In an alternative method, if the odor recognition apparatus 10 is connected to a laptop computer preloaded with a Fast Fourier Transform software program (such as SpectraPLUS™ Audio Spectrum Analyzer available from Pioneer Hill Software LLC, Poulsbo Wash., USA), the user operates the software in a Real Time Mode and visually adjusts each sensor null adjustment knob 1b, 2b, 3b, 4b, 5b, 6b, 7b, 8b, 9b, 10b, 11b, and 12b until the corresponding sensor peak is minimized or completely disappears in the software display. All of the sensor selection switches 1a, 2a, 3a, 4a, 5a, 6a, 7a, 8a, 9a, 10a, 11a, and 12a should be in the "ON" position if using this alternate method.

Figure 4:
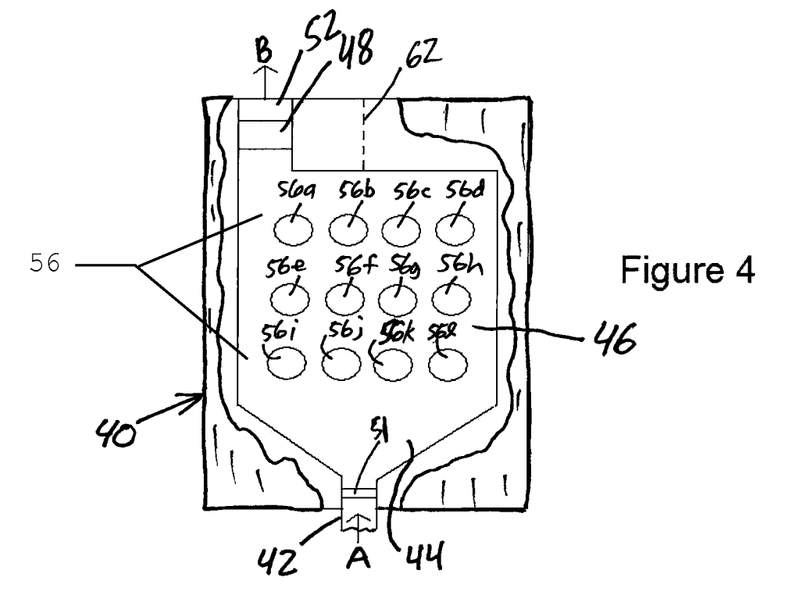
FIG. 4 is a top view of the detector head of the odor recognition apparatus of FIG. 1.

In the example embodiment, the odor recognition apparatus 10 offers multiple sample flow rate adjustments for maximum odor detection at varying heights and under different operating conditions. Users can adjust the fan speed using fan speed knob 16 from 0 to 10 depending on the environmental conditions. Each fan speed corresponds to a flow rate, ranging from 33 L/min to 83 L/min. This adjustment allows users to select the amount of air sample that flows across the sensors 56a, 56b, 56c, 56d, 56e, 56f, 56g, 56h, 56i, 56j, 56k and 56l. The following Table 1 presents non-limiting example fan speeds and corresponding flow rates.

TABLE 1

| Fan Speed | Flow Rate (L/min) |
| --- | --- |
| OFF | 0 |
| 1 | 33 |
| 2 | 39 |
| 3 | 44 |
| 4 | 50 |
| 5 | 55 |
| 6 | 61 |
| 7 | 64 |
| 8 | 77 |
| 9 | 80 |
| 10 | 83 |

Additionally, the non-limiting preferred settings for varying heights above the ground are presented in Table 2. In general, the odor recognition apparatus 10 functions well at a medium flow rate (55-61 L/min or Fan Speed 5-6) with the nozzle 42 of the detector head 40 located close to the surface (0-2" above ground). The preferred settings were determined in the laboratory by placing the detector head 40 at varying heights above a point source of 10% ethanol.

TABLE 2

Fan Speed Settings At Varying Heights Above The Surface (in Inches).

| Height Above Surface (in) | Fan Speed | Flow Rate (L/min) |
| --- | --- | --- |
| 0" | 5-6 | 55-61 |
| 2" | 5-6 | 55-61 |
| 4" | 8 | 77 |

The preferred fan speed settings can be greatly impacted by the ambient wind speed at the immediate location of the detector head 40. If the odor recognition apparatus 10 is exposed to high wind movement in the field, it may be necessary to increase the fan speed to compensate. In addition, it might be necessary to attach a wind screen to the nozzle 42 of the detector head 40. This attachment will help to compensate for a variety of field sampling conditions so as to help eliminate any potential interference in the signal response. The odor recognition apparatus 10 is a chemical vapor/soil gas detector and as a result, will perform best in the field under environmental conditions that are favorable for the emission of soil gas vapors from the ground. Early morning and mid-morning hours are likely a good choice as the ground begins heating up from exposure the sun and warmer air.

Once the odor recognition apparatus 10 has been zeroed and properly adjusted, it will be ready for detecting chemical vapors. A user proceeds by walking at a slow pace carrying the odor recognition apparatus 10 over the target search area with the nozzle 42 of the detector head 40 preferably located 1 or 2 inches above the ground (if possible). As a user walks, the user slowly moves the detector head 40 back and forth in a sweeping motion while maintaining the distance from the surface of the ground as close as possible. The fan speed can be adjusted fan speed according to height off ground as in Table 2. If the odor recognition apparatus 10 encounters chemical vapors, it should respond within a few seconds. Preferably, a user remains at the same location for at least 10-30 seconds to register a stable chemical signature. If the odor recognition apparatus 10 reacts to a particular point of origin, the user should consider digging a small hole and placing the detector head 40 inside the hole. This will allow the odor recognition apparatus 10 to record a better signature of the chemicals in the soil and may help narrow down the location of the clandestine grave. After the odor recognition apparatus 10 responds to a particular source, it should be removed from the chemical vapors, and sufficient time should be provided for the sensors 56a, 56b, 56c, 56d, 56e, 56f, 56g, 56h, 56i, 56j, 56k and 56l to return to zero before moving to a new area. If an excessive amount of time is required for the sensors 56a, 56b, 56c, 56d, 56e, 56f, 56g, 56h, 56i, 56j, 56k and 56l to return to zero, the operator may need to re-zero the instrument in a clean location.

In most cases, correctly zeroing the odor recognition apparatus 10 in the ambient environment should reduce the frequency of false positives due to environmental influences such as vegetation, animal bones, and waste; however, the user should periodically check to make sure the odor recognition apparatus 10 is zeroed. Additionally, the operator should preferably be alert to potential sources of chemical vapors (containers, strong odors, dead animals, etc.) that could lead to a false indication.

The odor recognition apparatus 10 is intended to detect the volatile chemicals associated with clandestine graves and provide visual and audible signals when a grave is encountered. When the odor recognition apparatus 10 'sniffs' a particular odor, it will display a unique pattern on the sensor response display 12 of the main output head 11 as well as produce a unique sound through the speakers 28, 29. The visual patterns of many standard chemicals, accelerants, explosives, and controlled substances have been documented for reference purposes. Although the exact signature and amplitude may vary slightly depending on environmental conditions, the general pattern should remain constant.

Generally, most users will find the visual patterns to be easier to recognize; however, if desired, users can plug headphones into the audio output jack 27 on the audio output module 20 and listen to the audio signal. Each chemical (and combination of chemicals) will produce a unique sound, allowing the user to identify graves by the audio pattern alone. The recording feature of the odor recognition apparatus 10 allows the user to save the signal output for further processing in the laboratory. The audio signal can be recorded easily using a handheld digital recorder or an external laptop computer with an audio input port and sound recording software. The user connects the recording device to an auxiliary audio output jack on the back of the main output head 11 with an auxiliary cord. These recordings can be analyzed or processed on a computer with an audio analyzer program such as SpectraPLUS™ Professional. If using an external laptop to record the audio signal, any recording software such as Microsoft Windows Sound Recorder can be used; however, the files will need to be converted to a .wav file to be used in the SpectraPLUS software program.

Because each of the sensors 56a, 56b, 56c, 56d, 56e, 56f, 56g, 56h, 56i, 56j, 56k and 56l is modulated with a unique audio frequency sine wave, the response of each sensor can be easily recovered using a Fourier Transform routine. SpectraPLUS™ Professional is Fast Fourier Transform software, which allows the user to calibrate the odor recognition apparatus 10 more accurately, subtract background noise from the audio output, and analyze each audio signal's unique properties.

Before using the SpectraPLUS™ software with recorded data, the files must first be converted to a .wav file and the following settings should be configured before performing any activities within the program. The user opens the SpectraPLUS™ program, and clicks "View" on the upper toolbar, and ensures that a check-mark is beside "Spectrum". The user uses this particular window to zero the odor recognition apparatus 10 by turning the sensor null adjustment knobs 1b, 2b, 3b, 4b, 5b, 6b, 7b, 8b, 9b, 10b, 11b, and 12b until each peak disappears. The user clicks "Options" on the upper toolbar and then clicks "Scaling". The user selects "Linear" in the Amplitude Axis and the Frequency Axis boxes, and clicks OK. Next, the user clicks "Spectrum" under the "Options" drop-down menu (same as before). The user selects "Line graph" and sets Plot Top to "5" in the Plot Options box. The Plot Top can be adjusted later if needed. The user enters 100 Hz and 800 Hz for the Start and Stop frequencies in the Frequency Span box, and clicks OK. The SpectraPLUS™ program should now be ready for zeroing the odor recognition apparatus 10, recording audio signals, or analyzing recordings.

The odor recognition apparatus 10 can be connected to the computer running this software via the auxiliary audio output jack on the back of the main output head 11. In the SpectraPLUS™ program, the user clicks "Mode" on the upper toolbar, and selects "Real Time". The user clicks the RUN button located in the upper left corner. The user adjusts each of the sensor null adjustment knobs 1b, 2b, 3b, 4b, 5b, 6b, 7b, 8b, 9b, 10b, 11b, and 12b on the odor recognition apparatus 10 until each corresponding sensor peak in SpectraPLUS™ software program disappears. The user clicks 'STOP' when finished.

For recording, the odor recognition apparatus 10 can be connected to record audio signals with the SpectraPLUS™ program. The user switches to the "Recorder" mode (located on the "Mode" drop-down menu). The user clicks the RECORD button located in the upper left corner. If recording a specific location, the user first records approximately 15 seconds of background noise. The user clicks STOP when finished. The user save the audio file by clicking "Save" under the "File" drop-down menu. To review previously recorded files, the user opens the file from the "File" drop-down menu. The user clicks the PLAY button located in the upper left corner. Clicking the RECORD button will record any sound to the end of the opened file.

Example sensors useful in the sensors 56a, 56b, 56c, 56d, 56e, 56f, 56g, 56h, 56i, 56j, 56k and 56l of the odor recognition apparatus 10 of the invention are heatable metal oxide sensors. These metal oxide sensors include a semiconductor surface with an integral heater element. Examples of metal oxide semiconductor materials suitable for use in the heatable metal oxide sensors of apparatus include, but are not limited to, $SnO_2$, $ZnO$, $Fe_2O_3$, $TiO_2$, and $In_2O_3$. Such heatable metal oxide sensors are disclosed in, for example, U.S. Pat. No. 3,676,820 to Taguchi, the specification of which is hereby incorporated by reference in its entirety. Alternatively, such heatable metal oxide sensors can be purchased commercially from, for example, Figaro Engineering, Inc., Arlington Heights, Ill., USA.

Non-limiting examples of Taguchi heatable metal oxide sensors from Figaro Engineering which are suitable for use in the odor recognition apparatus 10 described herein, and the chemical compounds detected are listed below in Table 3.

TABLE 3

Examples of Taguchi Heatable Metal Oxide Sensors from Figaro Engineering and Chemical Compounds Detected

| Sensor | Figaro TGS | Chemicals Detected |
|---|---|---|
| 56a | 813 | CG[1]: LP-Gas, Propane, General Combustible Gases |
| 56b | 822 | Organic Solvents, Alcohol, Toluene, Xylene, Other volatile organic vapors |
| 56c | 842 | CG[1]: Natural gas, Methane |
| 56d | 830 | CFCs[2] (HCFCs[3] & HFCs[4]): R-22, R-113 |
| 56e | 831 | CFCs[2] (HCFCs[3] & HFCs[4]): R-22, R-21 |
| 56f | 832 | CFCs[2] (HCFCs[3] & HFCs[4]): R-22, R-134a |
| 56g | 883T-84Z | Water Vapors from Food |
| 56h | 825 | Toxic Gas: Hydrogen Sulfide |
| 56i | 813 | CG[1]: LP-Gas, Propane, General Combustible Gases |
| 56j | 826 | Toxic Gas: Ammonia Gas |
| 56k | 800 | Indoor Pollutants, Air Contaminants |
| 56l | 821 | Hydrogen Gas |

[1]CG—Combustible Gas.
[2]CFCs—Chlorofluorocarbons.
HCFCs[3]—Hydrochlorofluorocarbons.
HFCs[4]—Hydrofluorocarbons; R-22, R-113, R-21 and R-134a are halogenated refrigerant gases and LP-gas is "liquified petroleum gas" which is primarily a mixture of propane and butane.
TGS = Taguchi Gas Sensor When a gas molecule is absorbed on the surface of the metal oxide semiconductor materials, the sensor exhibits a change in electrical conductivity. Depending on the given metal oxide sensor utilized and gas molecule detected, the electrical conductivity can increase or decrease. In one embodiment, the electrical conductivity of a given metal oxide sensor is increased upon detection of a particular gas molecule. In another embodiment, the electrical conductivity of a given metal oxide sensor decreases upon detection of a particular gas molecule. The gas molecule detected can be any one of the chemical compounds liberated during the human decomposition process, such as those described above.

Different sensors are designed to have a greater response to particular chemicals or classes of chemical compounds based on the chemical formulation of the metal oxide sensor material and the temperature at which it is operated. Heatable metal oxide sensors, however, can respond to a wide range of chemical vapors. Accordingly, in one embodiment, an array of heatable metal oxide sensors is used in the odor recognition apparatus 10 of the invention as opposed to one or two sensors. As used herein, the term "array" refers to at least two.

In principle, the greater the number of unique sensors, the greater the specificity will be for a particular chemical vapor when the pattern of the collective sensors is used for identification. Therefore, in one embodiment, the heatable metal oxide sensor array contains at least three, four, five, six, seven or more, etc. heatable metal oxide sensors. Any number of heatable metal oxide sensors can be used in the array provided that the odor recognition apparatus 10 is light-weight and portable for use in the field. The term "light-weight" as used herein means that the apparatus is portable. For instance, the apparatus can be carried and held by a human. For example, the array can contain ten, eleven twelve, thirteen or more heatable metal oxide sensors.

Each heatable metal oxide sensor 56a, 56b, 56c, 56d, 56e, 56f, 56g, 56h, 56i, 56j, 56k and 56l in the array of the odor recognition apparatus 10 is modulated with a unique audio frequency. The audio frequency sine wave at the output of the metal oxide sensor is fed into a load resistor that is nominally the same resistance as that of the metal oxide sensor which creates a voltage divider circuit. When the sensor responds to the presence of a vapor, the resistance of the sensor decreases and causes the voltage level at the load resistor to increase in amplitude. Normally, the output of the sensor is nulled by feeding the output of the load resistor into one input of a differential amplifier. The other input of the differential amplifier is connected to a sine wave of the same phase and frequency as that applied to the sensor. A variable resistor allows the voltage of this sine wave to be manually adjusted to equal the voltage output of the load resistor which in turn nulls the output of the differential amplifier. When the sensor is exposed to a vapor that it is sensitive to, the null condition of the differential amplifier is overcome and a sine wave appears at the output of the differential amplifier. This output is further amplified and applied to an audio speaker, headphones, computer or the input of the bar graph driver. The sine waves are produced in the oscillator module 30.

Generally, the audio frequency utilized is capable of being detected by the human ear. For example, each heatable metal oxide sensor 56a, 56b, 56c, 56d, 56e, 56f, 56g, 56h, 56i, 56j, 56k and 56l can be modulated with one of twelve unique audio frequencies ranging from, for example, 220 Hz (key 37 on the piano, A3) to 659.255 Hz (key 56 on the piano, E5). The audio frequency signals for modulating the sensors are pure sine waves (i.e., single frequency with no harmonics) which are offset with a direct current (DC) voltage to provide drive signals that are always positive with respect to signal ground. Each sine wave is buffered with parallel amplifiers to provide two identical signals. One signal is applied to the input of the sensor and the other signal is a reference signal used in the detection scheme. The output of the heatable metal oxide sensor is fed into a variable load resistor that is connected to the signal ground path. The voltage developed across the load resistor varies with exposure of the heatable metal oxide sensor to various chemical vapors.

In another embodiment of the odor recognition apparatus 10 of the invention, the odor recognition apparatus 10 has Global Positioning System (GPS) capability and/or a wireless link to a computer. Preferably, the computer is located nearby. In this manner, a team of searchers, each with their own apparatus can perform a grid search and produce a map of concentration(s) of various chemical vapor(s) detected. The computer can archive the information, and perform further analysis based on developed models, and relay the data to other sites. In this embodiment of the odor recognition apparatus 10, a GPS receiver is mounted on the odor recognition apparatus 10. The receiver uses the GPS to provide exact and continually updated information concerning the position of the odor recognition apparatus 10 in global coordinates. Such receivers are commercially available, and may include differential correction methods to integrate data from a number of satellites and reference stations. The receiver can receive from GPS satellites and provide the correct latitude, longitude and altitude of the odor recognition apparatus 10, along with the precise time and date, and the speed and track over the ground of the apparatus. Such data can then be transmitted to a processor on the odor recognition apparatus 10. The processor may be any type of processor which can receive the required data and process it. The processor also receives data on the concentration levels of the chemical vapors detected. As the odor recognition apparatus 10 passes over the ground, the process transmits to the computer, by wireless link, signals including position data and concentration levels of the chemical vapors detected associated with each position such that the concentration levels of the chemical vapors detected at each position can be reviewed after the odor recognition apparatus 10 is directed over the ground.

Therefore, the invention provides a portable, chemical sensor capable of detecting clandestine burial sites of human remain and provides a method for detecting clandestine burial sites of human remains and for mapping the chemical vapor plume associated with these types of volatile sources. The invention may be used by law enforcement agencies interested in finding the bodies of murder victims, etc. The invention may also be used to locate bodies in earthquake ruins and collapsed buildings. In this regard, the term "burial sites of human remains" as used herein include burial sites that occur from, for instance, natural disaster and a collapsed building.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained therein.

What is claimed is:

1. An odor recognition apparatus comprising:
an air intake conduit;
an array of chemical sensors positioned in the air intake conduit to contact air in the air intake conduit;
a chemical detection circuit associated with and in electrical communication with each of the chemical sensors, each of the chemical sensors receiving an input signal from its associated chemical detection circuit, each chemical detection circuit generating an output signal derived from its associated input signal and a chemical detection signal generated by its associated chemical sensor, and
an electronic mixer for modulating the output signals generated by the chemical detection circuits,
wherein a first output signal from a first of the chemical detection circuits associated with one of the chemical sensors before application to an audio device has a different audio frequency than a second output signal from a second of the chemical detection circuits associated with another of the chemical sensors before application to an audio device.

2. The apparatus of claim 1 wherein:
the apparatus includes a display in electrical communication with each chemical detection circuit, and
a representation of each output signal is individually displayed on the display.

3. The apparatus of claim 1 wherein:
each input signal has a unique audible frequency, and
each chemical detection circuit generates an output signal having a frequency the same as its associated input signal.

4. The apparatus of claim 3 wherein:
the output signal of each chemical detection circuit has a frequency corresponding to a musical note.

5. The apparatus of claim 4 wherein:
the output signal of each chemical detection circuit has a loudness proportional to the chemical detection signal generated by its associated chemical sensor.

6. The apparatus of claim 1 wherein:
each input signal is a sine wave containing only a single frequency component with no harmonic components.

7. The apparatus of claim 1 further comprising:
means for adjusting an amplitude of each input signal.

8. The apparatus of claim 1 wherein:
each input signal can be offset with either a positive voltage or a negative voltage with respect to signal ground.

9. The apparatus of claim 1 wherein:
the output signal of each chemical detection circuit has an amplitude proportional to the chemical detection signal generated by its associated chemical sensor.

10. The apparatus of claim 1 further comprising:
means for drawing an air stream through the air intake conduit,
wherein the array of chemical sensors is positioned in the air intake conduit to contact the air stream drawn through the air intake conduit.

11. The apparatus of claim 10 wherein:
the means for drawing an air stream through the air intake conduit includes means for varying a flow rate of the air stream.

12. The apparatus of claim 1 wherein:
the chemical sensors are selected from heated metal oxide sensors, capacitive sensors, light emitting diode/photo diode sensors, catalytic bead sensors, solid-state sensors, resistive sensors, thermocouples, thermal resistors, and platinum resistors.

13. The apparatus of claim 1 wherein:
the output signal of each chemical detection circuit is electronically mixed to produce a composite signal.

14. The apparatus of claim 13 further comprising:
a data storage device,
wherein the composite signal is digitized and stored in the data storage device in a file structure that can be converted to a format that is compatible with a Fast Fourier Transform software program.

15. The apparatus of claim 14 wherein:
the Fast Fourier Transform software program recovers the output signal of each chemical detection circuit by performing a Fast Fourier Transform on the composite signal.

16. The apparatus of claim 13 further comprising:
a data storage device,
wherein the composite signal is digitized and stored in the data storage device in a file structure that can be converted to a format that is compatible with an audio processing software program that can recover the output signal of each chemical detection circuit.

17. The apparatus of claim 1 further comprising:
an audio speaker,
wherein the output signal of each chemical detection circuit has a frequency corresponding to a musical note, and
wherein the output signal of each chemical detection circuit comprises an audio signal that drives the audio speaker.

18. The apparatus of claim 1 wherein:
each chemical detection circuit includes means for manually nulling the chemical detection signal of each of the sensors in an atmosphere that contains levels of chemical vapors.

19. The apparatus of claim 1 wherein:
each chemical detection circuit includes at least one of a temperature compensation circuit or a humidity compensation circuit.

20. The apparatus of claim 1 further comprising:
at least one of a metal detector, a video camera and video recording device, an infrared video camera and recorder, a thermal imaging camera and recorder, an audio probe, a soil resistance probe, means for detecting fluorescence from bones, fragments of bones, or teeth, or a LASER Induced Breakdown spectrometry probe.

21. The apparatus of claim 1 wherein:
the chemical sensors include at least one heated metal oxide sensor, and at least one of the following: an electrochemical sensor, a capacitive sensor, a catalytic bead sensor, an infrared chemical sensor, a visible-light chemical sensor, a solid-state chemical sensor, a surface acoustic wave chemical sensor, a coated piezo-electric sensor, an ionization-type chemical sensor, a colorimetric chemical sensor, and a spectroscopic chemical sensor.

22. The apparatus of claim 1 further comprising:
a source of clean air for nulling the chemical detection signal of each of the sensors in an atmosphere that contains levels of chemical vapors.

23. A method for detecting a burial site of human remains, the method comprising:
providing the apparatus of claim 1;
displaying a representation of each output signal on a display; and
monitoring the representation of each output signal on the display to determine that an odor is present in the air in the air intake conduit, the odor indicating a burial site of human remains.

24. A method for detecting a burial site of human remains, the method comprising:
providing the apparatus of claim 1;
driving an audio speaker with an audio signal comprising the output signal of each chemical detection circuit; and
monitoring sound from the audio speaker to determine that an odor is present in the air in the air intake conduit, the odor indicating a burial site of human remains.

25. A method for detecting a burial site of human remains, the method comprising:
providing the apparatus of claim 1;
electronically mixing the output signal of each chemical detection circuit to produce a composite signal;
digitizing and storing the composite signal in a data storage device in a file structure that can be converted to a format that is compatible with a Fast Fourier Transform software program;
recovering the output signal of each chemical detection circuit by performing a Fast Fourier Transform on the composite signal using the Fast Fourier Transform software program; and
reviewing each recovered output signal to determine that an odor is present in the air in the air intake conduit, the odor indicating a burial site of human remains.

26. A method for detecting a burial site of human remains, the method comprising:
providing the apparatus of claim 1;
electronically mixing the output signal of each chemical detection circuit to produce a composite signal;
digitizing and storing the composite signal in a data storage device in a file structure that can be converted to a format that is compatible with an audio processing software program;
recovering the output signal of each chemical detection circuit using the audio processing software program; and
reviewing each recovered output signal to determine that an odor is present in the air in the air intake conduit, the odor indicating a burial site of human remains.

* * * * *